(12) United States Patent
Hoyt et al.

(10) Patent No.: US 8,199,999 B2
(45) Date of Patent: Jun. 12, 2012

(54) IMAGE CLASSIFIER TRAINING

(75) Inventors: Clifford C. Hoyt, Wellesley, MA (US); Richard Levenson, Brighton, MA (US)

(73) Assignee: Cambridge Research & Instrumentation, Inc., Woburn, MA (US)

( * ) Notice: Subject to any disclaimer, the term of this patent is extended or adjusted under 35 U.S.C. 154(b) by 472 days.

(21) Appl. No.: 12/486,718

(22) Filed: Jun. 17, 2009

(65) Prior Publication Data

US 2009/0324051 A1  Dec. 31, 2009

Related U.S. Application Data (60) Provisional application No. 61/073,222, filed on Jun. 17, 2008.

(51) Int. Cl.
*G06K 9/00* (2006.01)
*G06K 9/62* (2006.01)

(52) U.S. Cl. .......................... 382/133; 382/159

(58) Field of Classification Search .................. 382/133, 382/159, 173, 224
See application file for complete search history.

(56) References Cited

U.S. PATENT DOCUMENTS

| | | | |
|---|---|---|---|
| 5,521,705 A | 5/1996 | Oldenbourg et al. | |
| 5,539,517 A | 7/1996 | Cabib et al. | |
| 5,784,162 A | 7/1998 | Cabib et al. | |
| 5,991,028 A | 11/1999 | Cabib et al. | |
| 5,995,645 A * | 11/1999 | Soenksen et al. | 382/133 |
| 6,007,996 A | 12/1999 | McNamara et al. | |
| 6,055,325 A * | 4/2000 | Garini et al. | 382/129 |
| 6,142,629 A | 11/2000 | Adel et al. | |
| 6,373,568 B1 | 4/2002 | Miller et al. | |
| 6,421,131 B1 | 7/2002 | Miller | |
| 6,466,687 B1 | 10/2002 | Uppaluri et al. | |
| 6,478,732 B2 * | 11/2002 | Adachi | 600/178 |
| 6,690,466 B2 | 2/2004 | Miller et al. | |
| 6,776,760 B2 | 8/2004 | Marmarelis | |
| 6,920,239 B2 | 7/2005 | Douglass et al. | |
| 6,924,893 B2 | 8/2005 | Oldenbourg et al. | |
| 2003/0081204 A1 | 5/2003 | Cronin et al. | |

(Continued)

FOREIGN PATENT DOCUMENTS

WO  WO 98/43042  10/1998

(Continued)

OTHER PUBLICATIONS

Selim Aksoy et al., "Textural Features for Image Database Retrieval", IEEE, pp. 45-49 (1998).

(Continued)

*Primary Examiner* — Daniel Mariam
(74) *Attorney, Agent, or Firm* — Fish & Richardson P.C.

(57) ABSTRACT

Methods are disclosed that include: (a) applying a first stain to a first sample having a plurality of regions, where the first stain selectively binds to only a first subset of the regions of the first sample; (b) applying a second stain to the first sample, where the second stain binds to a second set of regions of the first sample; (c) obtaining an image of the first sample, and analyzing the image to obtain a first component image corresponding substantially only to spectral contributions from the first stain, and a second component image corresponding substantially only to spectral contributions from the second stain; and (d) training a classifier to identify regions of a second sample based on information derived from the first and second component images, the identified regions corresponding to the first subset of regions of the first sample.

70 Claims, 2 Drawing Sheets

U.S. PATENT DOCUMENTS

| | | | |
|---|---|---|---|
| 2003/0138140 | A1 | 7/2003 | Marcelpoil et al. |
| 2003/0223248 | A1 | 12/2003 | Cronin et al. |
| 2005/0065440 | A1 | 3/2005 | Levenson |
| 2006/0082762 | A1 | 4/2006 | Leverette et al. |
| 2006/0119865 | A1 | 6/2006 | Hoyt et al. |
| 2006/0245631 | A1 | 11/2006 | Levenson et al. |
| 2007/0016082 | A1 | 1/2007 | Levenson et al. |
| 2007/0231784 | A1 | 10/2007 | Hoyt et al. |
| 2008/0074644 | A1 | 3/2008 | Levenson et al. |
| 2008/0074649 | A1 | 3/2008 | Levenson et al. |
| 2009/0226059 | A1 | 9/2009 | Levenson et al. |
| 2009/0257640 | A1 | 10/2009 | Gossage et al. |
| 2010/0075373 | A1 | 3/2010 | Hoyt |
| 2011/0182490 | A1 | 7/2011 | Hoyt et al. |

FOREIGN PATENT DOCUMENTS

| | | |
|---|---|---|
| WO | WO 2005/040769 | 5/2005 |
| WO | WO 2006/081547 | 8/2006 |
| WO | WO 2008/039758 | 4/2008 |

OTHER PUBLICATIONS

Bishop, Christopher M., "The Multi-Layer Perceptron", Neural Networks for Pattern Recognition (Oxford University Press, 1995), pp. 116-163.

Kenneth P. Camilleri et al., "Spectral Unmixing of Mixed Pixels for Texture Boundary Refinement", IEEE, pp. 1084-1087 (2000).

Haralick, R.M. et al., "Textural features for image classification", IEEE Transactions on Systems, Man, and Cybernetics, vol. SMC-3: 610-621 (1973).

Jimenez, L. et al., "Hyperspectral Data Analysis and Feature Reduction Via Projection in Pursuit", IEEE Transactions on Geoscience and Remote Sensing 37(6): 2653-2667 (1999).

Paul M. Mather, "Classification 'What is or is not a cow is for the public to decide'", *Computer Processing of Remotely-Sensed Images: An Introduction, Third Edition*, John Wiley & Sons, Ltd. (2004).

Stephen W. Wharton, "A Contextual Classification Method for Recognizing Land Use Patterns in High Resolution Remotely Sensed Data", *Pattern Recognition*, vol. 15, No. 4, pp. 317-324 (1982).

Chinese Office Action for Application No. 200680010148.7 dated Dec. 19, 2008.

Chinese Office Action for Application No. 200680010148.7 dated Jul. 3, 2009.

European Office Action for Application No. 06 719 860.6, dated Nov. 7, 2007.

European Office Action/Summons to Attend Oral Proceedings for Application No. 06719 860.6, dated Feb. 3, 2011.

International Search Report and Written Opinion for International Application No. PCT/US2006/003197, dated May 22, 2006.

Chinese Office Action for Application No. 201010164482.6, dated Jun. 30, 2011.

* cited by examiner

IMAGE CLASSIFIER TRAINING

CROSS-REFERENCE TO RELATED APPLICATIONS

This application claims priority to U.S. Provisional Application Ser. No. 61/073,222, filed on Jun. 17, 2008, the entire contents of which are incorporated herein by reference.

TECHNICAL FIELD

This disclosure relates to sample imaging and classification.

BACKGROUND

Automated machine-based classifiers can be used to identify features of interest in a sample based on one or more sample images. Classifier training can be a time-consuming process and can be prone to operator error.

SUMMARY

In a first aspect, the disclosure features a method that includes: (a) applying a first stain to a first sample having a plurality of regions, where the first stain selectively binds to only a first subset of the regions of the first sample; (b) applying a second stain to the first sample, where the second stain binds to a second set of regions of the first sample; (c) obtaining an image of the first sample, and analyzing the image to obtain a first component image corresponding substantially only to spectral contributions from the first stain, and a second component image corresponding substantially only to spectral contributions from the second stain; and (d) training a classifier to identify regions of a second sample based on information derived from the first and second component images, the identified regions corresponding to the first subset of regions of the first sample.

Embodiments of the method can include any of the following features.

The first subset of regions and the second set of regions can have regions in common. The second set of regions can include at least some regions that are each adjacent to a region in the first subset. The second set of regions can be a subset of the regions of the first sample. The second set of regions can correspond to substantially all of the first sample. The first subset of regions can correspond to membranes in the first sample. The second set of regions can correspond to nuclei in the first sample. The second set of regions can correspond to non-specific binding sites in the first sample.

The information derived from the first component image can include position information corresponding to the first subset of regions. The information derived from the first component image can include information about an amount of the first stain in the first subset of regions. The information derived from the second component image can include information about an amount of the second stain in the second set of regions.

The method can include applying a third stain to the first sample, where the third stain selectively binds to a third subset of the regions of the first sample. The first subset of regions and the third subset of regions can have regions in common. The third subset of regions and the second set of regions can have regions in common. The second set of regions can include at least some regions that are each adjacent to a region in the third subset of regions.

The method can include analyzing the image to obtain a third component image, where the third component image corresponds substantially only to spectral contributions from the third stain, and training the classifier based on information derived from the third component image.

The second stain can include a counterstain.

The method can include applying a fourth stain to the first sample, where the fourth stain binds to a fourth set of regions of the first sample. The fourth set of regions can be a subset of regions of the first sample. The fourth set of regions can correspond to substantially all of the first sample. The method can include analyzing the image to obtain a fourth component image, where the fourth component image corresponds substantially only to spectral contributions from the fourth stain, and training the classifier based on information derived from the fourth component image.

The classifier can be a first classifier, and the method can include training a second classifier to identify regions of another sample, the identified regions corresponding to the third subset of regions of the first sample.

The first subset of regions of the first sample can include one or more types of tissue. The first subset of regions of the first sample can include one or more types of cells.

One of the first and second stains can include a fluorogenic stain and the other of the first and second stains can include a chromogenic stain. The first stain can include at least one member of the group consisting of immunohistochemical agents, cytokeratin, cadherin, DAB, fast red, fluorescein, rhodamine, Texas red, Cy3, Cy5, Cy5.5, Alexa dyes, and quantum dots. The second stain can include at least one member of the group consisting of DAPI, Hoechst blue, and hematoxylin.

Analyzing the image can include unmixing the image to obtain the first and second component images. Analyzing the image can include separating image color channels to obtain the first and second component images.

A difference between a wavelength of a maximum in a fluorescence emission spectrum of the first stain and a wavelength of a maximum in a fluorescence emission spectrum of the second stain can be 50 nm or more. A difference between a wavelength of maximum absorption of the first stain and a wavelength of maximum absorption of the second stain can be 50 nm or more.

The method can include obtaining birefringence information about the first sample, and training the classifier based on the birefringence information. The birefringence information can include one or more birefringence images of the first sample.

The method can include providing position information corresponding to the first subset of regions of the first sample to the classifier to train the classifier. The position information can include an image of the first sample that does not correspond to spectral contributions from the first stain. The position information can include texture information derived from the image of the first sample.

Obtaining the image can include exposing the first sample to incident radiation and detecting emitted radiation from the first sample, the emitted radiation corresponding to fluorescence emission from the first sample, reflected incident radiation from the first sample, or transmitted incident radiation from the first sample.

The method can include using the trained classifier to identify the regions of the second sample.

Embodiments of the method can also include any of the other method steps or features disclosed herein, as appropriate.

In another aspect, the disclosure features a method that includes: (a) applying a stain to a first sample having a plurality of regions, where the stain selectively binds to a first set of regions of the first sample; (b) obtaining an image of the first sample, and analyzing the image to obtain a component image corresponding substantially only to spectral contributions from the stain; (c) obtaining a birefringence image of the first sample; and (d) training a classifier to identify regions of a second sample based on information derived from the component image and the birefringence image.

Embodiments of the method can include any of the following features.

The first set of regions can be a subset of the regions of the first sample. The first set of regions can correspond to substantially all of the first sample.

The birefringence image can include a set of regions corresponding to a second subset of the regions of the first sample, the second subset of regions of the first sample having optical retardance values that are different from optical retardance values of other regions of the first sample. The second subset of regions and the first set of regions can have regions in common.

The first set of regions can include at least some regions that are each adjacent to a region in the second subset of regions. The second subset of regions can correspond to membranes in the first sample. The second subset of regions can correspond to nuclei in the first sample.

The information derived from the birefringence image can include position information corresponding to the second subset of regions.

The second subset of regions can include one or more types of tissue. The second subset of regions can include one or more types of cells. The second subset of regions can include one or more types of sub-cellular components.

The stain can include a counterstain.

Analyzing the image can include unmixing the image to obtain the component image. Analyzing the image can include separating image color channels to obtain the component image.

The method can include applying a second stain to the first sample, where the second stain binds to a third set of regions of the first sample, analyzing the image to obtain a second component image corresponding to the second stain, and training the classifier based on information derived from the second component image. The second stain can include a counterstain.

The method can include using the trained classifier to identify the regions of the second sample.

Embodiments of the method can also include any of the other method steps or features disclosed herein, as appropriate.

In a further aspect, the disclosure features a method that includes: (a) applying a stain to a first sample having a plurality of regions, where the stain selectively binds to only a first subset of the regions of the first sample; (b) obtaining an image of the first sample, and analyzing the image to obtain a first component image corresponding substantially only to spectral contributions from the first stain, and a second component image corresponding substantially only autofluorescence contributions from the sample; and (c) training a classifier to identify regions of a second sample based on information derived from the first and second component images, the identified regions corresponding to the first subset of regions of the first sample.

Embodiments of the method can include any of the following features.

The method can include applying a second stain to the first sample, where the second stain selectively binds to a second subset of the regions of the first sample.

The method can include analyzing the image to obtain a third component image, where the third component image corresponds substantially only to spectral contributions from the second stain, and training the classifier based on information derived from the third component image. The information derived from the first component image can include position information corresponding to the first subset of regions. The information derived from the first component image can include information about an amount of the first stain in the first subset of regions.

The method can include using the trained classifier to identify the regions of the second sample.

Embodiments of the method can also include any of the other method steps or features disclosed herein, as appropriate.

In another aspect, the disclosure features an apparatus that includes an electronic processor configured to obtain the image of the first sample, analyze the image, and train the classifier according to any of the methods disclosed herein. Embodiments of the apparatus can include any of the features disclosed herein, as appropriate.

In a further aspect, the disclosure features an apparatus that includes an electronic processor configured to obtain the image of the first sample, analyze the image, obtain the birefringence image of the first sample, and train the classifier according to any of the methods disclosed herein. Embodiments of the apparatus can include any of the features disclosed herein, as appropriate.

Unless otherwise defined, all technical and scientific terms used herein have the same meaning as commonly understood by one of ordinary skill in the art to which this disclosure belongs. All publications, patent applications, patents, and other references mentioned herein are incorporated by reference in their entirety. In case of conflict, the present specification, including definitions, will control. In addition, the materials, methods, and examples disclosed herein are illustrative only and not intended to be limiting.

The details of one or more embodiments are set forth in the accompanying drawings and description. Other features and advantages will also be apparent from the description, drawings, and claims.

DESCRIPTION OF DRAWINGS

Like reference symbols in the various drawings indicate like elements.

DETAILED DESCRIPTION

Automated analysis of samples can be used for both qualitative inspection and quantitative determination of sample properties. For example, automated analysis of biological samples such as stained tissue sections can be used to measure the amount of one or more stains that are applied to, and are bound to, the samples. The applied stains can reveal, for example, one or more properties or states of the sample (e.g., tissue) or components thereof (e.g., cells). Analysis protocols can include, for example, identifying one or more selected regions of a sample from one or more images of the sample.

The regions can correspond to different types of cells and/or to cells having one or more particular types of sub-cellular compartments, for example. Quantitative measurements of the identified regions can provide information about the amount of one or more stains present in the identified regions.

Typically, analysis of sample images is performed by an automated classifier that has been trained to operate on images that are representative of the sample images. Automated classifiers can embody various types of machine learning algorithms, including genetic algorithms, neural networks, and vector support machines. Methods and systems for automated classification of sample images are disclosed, for example, in the following patents and patent applications, the entire contents of each of which are incorporated herein by reference: U.S. Pat. No. 7,555,155 to Richard Levenson et al., issued on Jun. 30, 2009; and U.S. patent application Ser. No. 12/401,430 to Kirk William Gossage et al., filed on Mar. 10, 2009. To ensure that throughput is high and to reduce or eliminate the effects of operator error, such automated classifiers can typically classify samples with little or no operator intervention once they have been properly trained. That is, once trained, the classifiers can identify portions of sample images corresponding to particular regions of a sample either fully automatically or semi-automatically. Once the portions of the images have been identified, the classifiers can also perform quantitative analyses corresponding to the regions of the sample with little or no operator intervention.

In some systems, automated classifiers are trained using manual methods. Typically, for example, a trained expert such as a pathologist manually selects regions of one or more images corresponding to particular regions of interest in a sample (e.g., particular types of cells, particular cellular components, particular tissue types and/or target structures), for example by drawing outlines around the regions on a display screen. In some types of samples, there may be several different types of cell components, tissue types, and/or structures of interest for the operator to manually select. The samples corresponding to the images classified manually by the operator may include one or more stains applied to the samples to delineate different regions in the samples (e.g., cancer cells versus stroma) and/or to delineate different portions of individual cells (e.g., cytoplasm and nuclei). Conventional counterstains that are typically applied to such samples provide contextual information to trained operators that the operators can use in manually classifying regions of the samples. Counterstains that can be used to stain such samples include hematoxylin and eosin, for example.

Classifier training can be prone to inaccuracies arising from differences in perception and conclusions among different operators—different operators might classify different pixel subsets of training images as belonging to different classes (e.g., different types of cells, different cellular components). Further, training automated classifiers using images that are manually classified can be time consuming. For example, to train a neural network-based classifier, many different images may have to be manually classified by a system operator, with multiple regions in each of the images carefully selected and indicated as belonging to one of the classes of interest (or not belonging to a class of interest). The set of images used to train the automated classifier typically includes a range of different types of regions of interest to effectively represent the bounds of the sample images to be automatically analyzed. To develop a training set of classified images, particularly when the samples under study are expected to include considerable variability (e.g., for tissue samples corresponding to clinical cancer sections), large numbers of regions corresponding to each sample class of interest (e.g., 100 or more regions) may be selected manually. If these regions are improperly selected, training of the automated classifier may be inaccurate, leading to inaccurate image analysis results.

Further, direct determination of regions of samples based on applied stains may not be possible. For example, suitable stain(s) may not be available for the tissue types under investigation. As an example, cytokeratin can be used to locate cytoplasm in breast cancer cells. In general, however, there are no cytokeratins that are universal, and that uniformly stain all breast cancer tissues. Instead, to identify cytoplasm in multiple different types of breast cancer cells, multiple different cytokeratins (e.g., selected from a list of about 20 cytokeratins) may be used. A more general method for identifying breast cancer cell membranes would be particularly useful, for example, in certain quantitative assessments where a computed metric corresponds to the percentage of membrane area where an applied stain is present, in each identified breast cancer cell. Unfortunately, the absence of generalized stains for such purposes hinders this method of analysis.

Some attempts to classify samples have involved the application of immunohistochemical (IHC) agents to the samples, which can target particular portions of samples due to particular molecular specificities and add high visual contrast to the targeted portions. Simple image analysis algorithms such as thresholding can then be used to identify the targeted portions in sample images. Such agents are available, for example, from HistoRX (New Haven, Conn.).

The use of IHC agents for this purpose is restricted by a number of considerations, however. In some samples, for example, only a limited number of IHC agents can be applied before specificity for particular portions is lost. Further, a significant fraction of the multiplexing bandwidth of microscopy systems used to obtain sample images may be dedicated to measurement of spectral responses of the applied IHC agents. As a result, these dedicated spectral channels are typically not available for obtaining other information, such as information about particular types of molecular expression within the sample. Thus, from both the perspective of IHC agent specificity and from spectral considerations, this approach can limit or reduce the amount of molecular information that can be obtained.

The methods and systems disclosed herein are designed to provide approaches to training automated classifier systems that reduce and/or eliminate the manual labor involved in classifying training image sets, and that are generally applicable to a wide variety of different sample types. To accomplish this, in some embodiments, the methods and systems include applying spectrally distinguishable stains in two different stain preparations to samples, and then acquiring spectral images of the samples. By performing spectral unmixing on the acquired images, at least two different component images can be obtained. The component images can then be used directly to train automated classifier systems.

Figure 1:
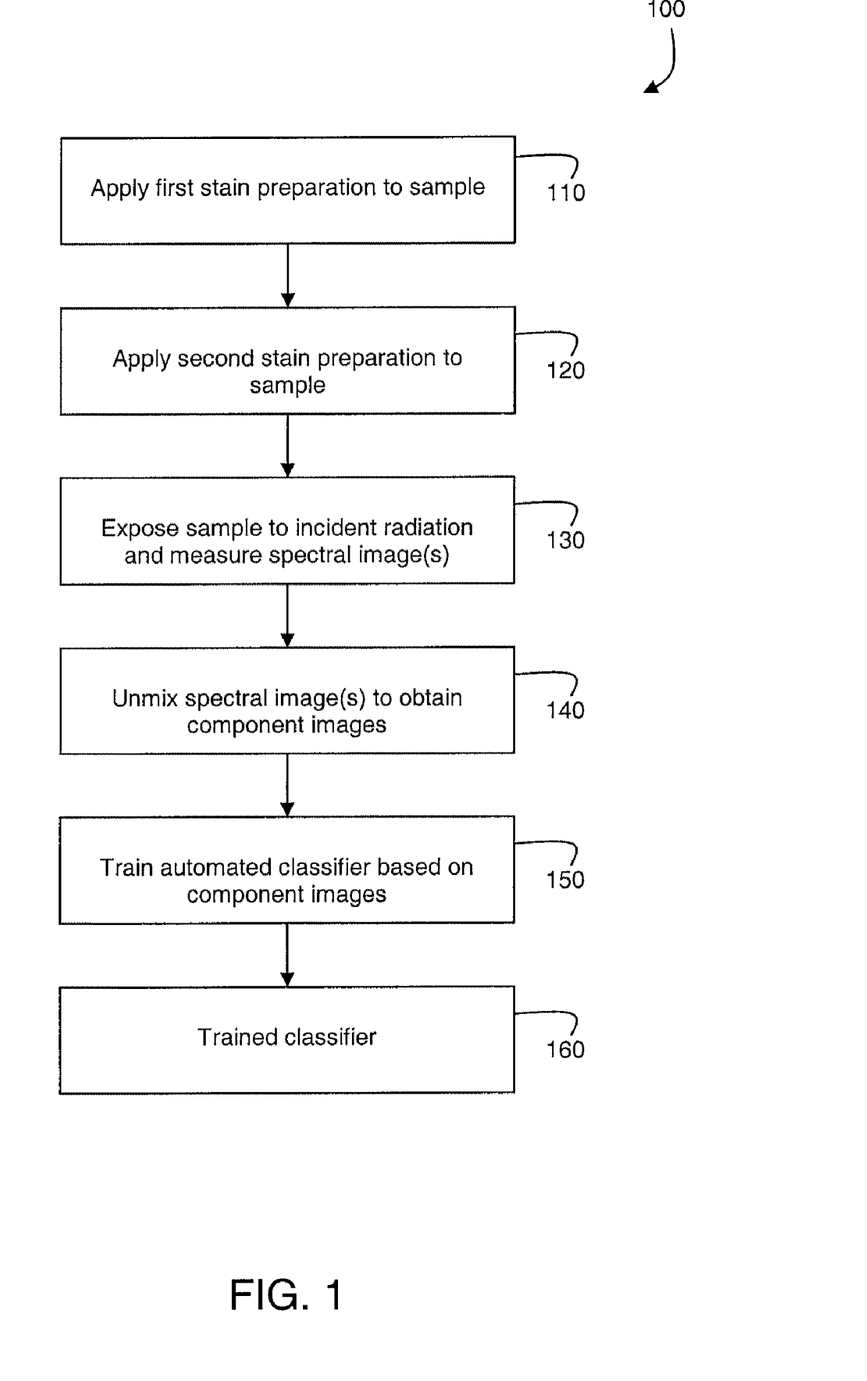
FIG. 1 is a flow chart showing steps in a procedure used to train an automated classifier.

FIG. 1 shows a flow chart 100 that includes a series of steps for training an automated classifier. In steps 110 and 120, two different stain preparations are applied to a training sample (e.g., a tissue section). In some embodiments, steps 110 and 120 can be combined so that the two stain preparations are applied in a single step. Typically, the stain preparations include applying stains that have different spectral and chemical properties. For example, the first stain preparation, which can include one or more individual steps, typically applies one or more regional markers to the sample; each of the applied regional markers selectively binds to particular regions of interest in the sample. Each of the regional markers in the first stain preparation is generally chosen so that it binds preferentially to one class of region of interest (e.g., where there is more than one class of region of interest) in the sample. Multiple different regional markers in the first stain preparation can be used to target different classes of regions of interest in the sample. In general, each of the different regional markers present in the first stain preparation are specific (e.g., bind preferentially) to a different particular type of region of interest in the sample. Regions of interest can include tissue structures, cells, sub-cellular compartments, and/or regions where chemical and/or biological agents are localized within the sample. By applying the first stain preparation to the sample, the regions of interest (or multiple classes or regions of interest) in the sample are delineated from other regions that are not of interest.

A wide variety of different markers can be used in the first stain preparation. Exemplary markers include, for example, IHC agents, one or more cytokeratins, cadherin, chromogenic markers such as DAB and/or fast red, fluorescent markers such as fluorescein, rhodamine, Texas red, Cy dyes such as Cy3, Cy5, and Cy5.5, Alexa dyes, and quantum dots that fluoresce at any selected wavelength. Mixtures of any of these agents can be used in combination in the first stain preparation. In particular, combinations of both fluorogenic and chromogenic agents can be used in the first stain preparation to identify specific regions of the sample. In some embodiments, some or all of the different markers used in the first stain may be applied more lightly than they would otherwise be applied in histological staining procedures to ensure that the various spectral contributions of the different markers can be separated from one another.

The second stain preparation typically includes one or more non-localized markers such as counterstains, and can include one or more staining steps to apply the non-localized markers to the sample. Exemplary non-localized markers that can be applied in the second stain preparation include hematoxylin, DAPI, and Hoechst blue. Although in FIG. 1 the second stain preparation is applied following the first stain preparation, more generally, the first and second stain preparations can be applied in any order. Further, in certain embodiments, application of the first and second stain preparations can be interleaved, such that steps involved in applying both regional markers and non-localized markers to the sample are performed in succession.

In some embodiments, the first and second stain preparations are selected such that some or all of the markers applied to the sample in each stain preparation are spectrally distinct. For example, the maxima in the total absorption or emission spectrum of the markers applied in the first and second stain preparations, respectively, can be separated by 5 nm or more (e.g., 10 nm or more, 20 nm or more, 30 nm or more, 50 nm or more, 75 nm or more, 100 nm or more, 200 nm or more, 300 nm or more).

In step 130 of flow chart 100, the stained sample (e.g., with the first and second stain preparations applied) is exposed to incident radiation, and one or more multispectral images (e.g., a spectral cube of data) corresponding to the sample is/are measured. The spectral cube corresponds to a plurality of two-dimensional images of the sample, with per-pixel spectrally resolved information extending along the third dimension of the cube. The spectrally resolved information can include, for example, sample absorption information as a function of wavelength, sample emission information as a function of wavelength, sample reflectance information as a function of wavelength, or other types of spectral information.

In step 140, the spectral cube is unmixed to obtain sample component images. In some embodiments, if the responses of particular markers applied in the first and second stain preparations are sufficiently separated from one another spectrally, the "unmixing" can be performed simply by examining different spectral sub-regions of the spectrally resolved information corresponding individually to the particular markers to obtain component images of the sample. In certain embodiments, the responses of the markers may partially overlap spectrally; the spectral overlap may even be significant or complete in some embodiments. To obtain component images, the spectral cube of data can be unmixed to obtain component images corresponding substantially only to contributions from the particular markers, respectively. Methods and systems for spectral unmixing are disclosed, for example, in the following patents and patent application publications, the entire contents of each of which are incorporated herein by reference: PCT Application No. PCT/US2004/031609 to Richard Levenson et al., filed on Sep. 23, 2004, published as WO 2005/040769; and U.S. Pat. No. 7,321,791 to Richard Levenson et al., issued on Jan. 22, 2008. Suitable systems for obtaining multispectral images of samples and performing unmixing of such images to obtain individual component images include the Nuance® system available from Cambridge Research & Instrumentation (Woburn, Mass.).

Although the preceding and subsequent discussion relates to acquiring spectral images of stained samples and unmixing the spectral images, other methods can also be used to obtain sample images that can be used to train automated classifiers, and to classify samples using trained classifiers. For example, one or more color images of a sample (e.g., red-green-blue ("RGB") images) can be acquired. Color images include different color channels (e.g., separate red, green, and blue channels) that can be independently analyzed, and the information from these separate channels can be used to train classifiers and classify samples using trained classifiers. Sample images corresponding to the individual color channels (or combinations of the channels) can form the component images that would otherwise be obtained from spectral unmixing (see the subsequent discussion of steps 140 and 150 in FIG. 1), particularly where regional markers applied in the first stain preparation are generally spectrally distinct from other regional and/or non-localized markers, and correspond spectrally to particular color channels. Alternatively, or in addition, the color channels (or color "planes") from one or more RGB image(s) can be used as the inputs to an unmixing step, to obtain component images. Accordingly, in the preceding and subsequent discussion, steps that involve acquiring spectral images and unmixing the images to obtain component images can include, alternatively or in addition, acquiring one or more color images and using images corresponding to different color channels, either with or without spectral unmixing of images corresponding to the different color channels, to train automated classifiers.

Spectral unmixing corresponds to a linear decomposition of an image or other data set into a series of contributions from different spectral contributors. Images of the stained samples disclosed herein will include multiple different contributions, including contributions from markers applied to the sample in each of the first and second stain preparations. Each of these contributions can be unmixed or decomposed into a separate spectral channel, forming an image of the stained sample that corresponds almost entirely to signal contributions from single spectral sources. When the contributions are unmixed into separate channels or images, signal strengths can be accurately quantified and analyzed.

The numerical spectral unmixing procedure will be described below for a tissue section that is stained with a single fluorescent stain. The equations can be generalized in straightforward fashion to include spectral contributions from multiple markers. The spectral data recorded at a given point (x,y) in an image depends on the amount of signal from the stain and on tissue autofluorescence as:

$$S(x,y,\lambda) = a(x,y)*F(\lambda) + b(x,y)*G(\lambda) \quad [1]$$

where (x, y) indices are used to denote a given pixel location in the image, the asterisk "*" denotes multiplication, $\lambda$ is used to denote a given wavelength of fluorescence emission or detection, and S(x, y, $\lambda$) denotes the net signal for a given location and wavelength, F($\lambda$) denotes the emission spectrum of autofluorescence, G($\lambda$) denotes the emission spectrum of the stain, a(x, y) indicates the abundance of autofluorescence signal at a given (x, y) location, and b(x, y) indicates the abundance of stain fluorescence at a given (x, y) location.

Equation [1] states that the net signal from a given location is the sum of two contributions, weighted by the relative amount of autofluorescence and stain fluorescence present. It is easier to see if one writes the above equation for a single pixel:

$$S(\lambda) = aF(\lambda) + bG(\lambda) \quad [2]$$

F and G may be termed the spectral eigenstates for the system, which are combined in various amounts according to the amount of autofluorescence and stain emission, to produce an observed spectrum S.

Now if the emission spectra of the autofluorescence and of the stain are known (or can be deduced), one may invert equation [2] by linear algebra to solve for a and b, provided that the spectrum S has at least two elements in it, i.e., that one has data for at least two emission wavelengths $\lambda$. Then we can write $$A = E^{-1}S \quad [3]$$

where

A is a column vector with components a and b, and

E is the matrix whose columns are the spectral eigenstates, namely [F G].

Using equation [3], one can take a captured spectral image (e.g., a spectral cube) and calculate the abundance of the autofluorescence and of the stain sources. This process can be repeated for each pixel in the image, to produce separate images of the sample that correspond substantially to autofluorescence only, and to stain fluorescence only, and are free of contributions from other spectral sources. Note that the matrix E need only be inverted once for a given set of autofluorescence and stain spectra, so the calculation of abundances is not burdensome and can be readily done in nearly real-time by a personal computer.

In some embodiments, when multiple stains are applied to a sample, the individual spectra (e.g., the spectral eigenstates discussed above) of the stains are different than the spectra of the stains applied individually to tissue sections. These changes can arise, for example, from chemical interactions between the various stains, and/or from environmental conditions during or after the staining protocol. As long as these changes can be quantitatively reproduced in control experiments to provide accurate spectral eigenstates for the unmixing algorithm, however, the individual contributions of these stains to spectral images of the sample can be deconvolved to obtain quantitative information about the absolute amount of each stain present in the tissue section.

Accordingly, by using the spectral unmixing methods discussed above in step 140 of flow chart 100, component images of the sample corresponding to regional and non-localized markers applied in the first stain preparation and in the second stain preparation, respectively, can be obtained. When the first stain preparation includes multiple regional markers (e.g., when the multiple regional markers are used to selectively stain different classes of regions of interest in the sample), the spectral unmixing process can yield separate component images corresponding substantially only to contributions from each of the single regional markers. When the second stain preparation includes multiple non-local markers, the spectral unmixing process can yield separate component images corresponding substantially only to contributions from each of the single non-localized markers.

Component images corresponding to regional markers applied to the sample in the first stain preparation identify where regions of interest in the sample are located. By identifying these regions through a combination of selective staining and spectral unmixing, the tedious, time-consuming step of manual classification of regions of interest in sample images to train an automated classifier can be reduced or eliminated. In embodiments where multiple different classes of regions of interest are present, each of the multiple unmixed component images corresponding to one of the regional markers applied in the first stain preparation can be used to identify portions of the sample corresponding a different one of the classes of regions of interest.

Component image(s) corresponding to one or more regional markers applied in the first stain preparation can be submitted to the automated classifier in step 150. Analysis of the component image(s), using techniques such as comparison against fixed and/or adaptive thresholds, can be used to establish regions of interest in the sample for training the classifier.

Component image(s) corresponding one or more non-localized markers applied in the second stain preparation can also be submitted to the automated classifier in step 150. The component image(s) corresponding to the non-localized marker(s) are analyzed using information delineating regions of interest from the one or more component images corresponding to regional markers applied in the first stain preparation to train the automated classifier in step 150 to classify regions in images that correspond to samples stained with non-localized markers such as those applied in the second stain preparation. For example, classification algorithms implemented in the automated classifier can be developed to determine whether each pixel in an image belongs to a particular class of region of interest, or even to one of several classes of regions of interest. Typically, information derived from component images corresponding to regional markers applied in the first stain preparation is used to identify regions of interest in sample images, and then the one or more component image(s) corresponding to non-localized markers applied in the second stain preparation (e.g., one or more counterstains) is/are used to train the automated classifier, guided by the identified regions of interest.

This training procedure, in step 160, yields a trained classifier, which can then be used to identify regions of interest in subsequent samples that have been stained, for example, only with non-localized markers such as those applied in the second stain preparation (e.g., one or more counterstains). Further, the trained classifier can be used to identify regions of interest in samples that have been stained using one or more regional markers; the regional markers can be the same as, or different from, regional markers that are applied in the first stain preparation. In some embodiments, for example, subsequent samples are not stained with regional markers such as those applied in the first stain preparation or with any other regional marker, but are instead stained with one or more non-localized stains such as one of more of the stains (e.g., counterstains) applied in the second stain preparation and/or one or more other non-localized stains. The trained automated classifier can identify and classify regions of interest in such samples based on component images corresponding to the applied non-localized stains (e.g., corresponding to one or more of the counterstains that were applied to the training sample in the second stain preparation).

Typically, the types of regions of interest in subsequent samples correspond to the types of regions of interest identified in the sample used to train the automated classifier. For example, the regions of interest in the training sample can include a first type of region of interest, such as a first type of tissue, for which a selective regional marker is available. The regional marker is applied to the training sample in the first stain preparation in flow chart 100, and a trained automated classifier is obtained in step 160. Subsequently, the trained automated classifier is used to analyze one or more samples that include a second type of regions of interest different from the first type of region of interest. The second type of regions of interest in the subsequent samples correspond to the first type of regions of interest in the training sample. This procedure can be used where no selective regional marker is readily available for the second type of region of interest. For example, in identifying and classifying certain types of cancers, one or more regional markers may be available for a first phenotype, and a training sample that includes the first phenotype can be used to train the automated classifier. Subsequently, samples that include a second phenotype that corresponds to, but is not identical to, the first phenotype can be analyzed using the trained automated classifier. Although the regions of interest in the training sample and the subsequent samples are of different types, if they are sufficiently related, then the automated classifier can still be used to identify the subsequent samples. As a result, cells, sub-cellular components, structures, and other sample features for which no selective regional marker is reliably available can nonetheless readily be identified and analyzed.

In certain embodiments, the training procedure shown in flow chart 100, implemented by applying a particular set of regional markers to a training sample in the first stain preparation, can yield a trained automated classifier that is capable of identifying and analyzing regions of interest in subsequent samples to which different regional markers have been applied. The different regional markers may not be applied for purposes of training the classifier, but can instead be applied to selectively stain certain portions of the samples for visual analysis, or for automated analysis using simple methods such as thresholding detection. This procedure can be used in situations where the subsequent samples have a range of variability that might otherwise require applying multiple different regional markers and/or might otherwise require selection among several different regional markers to properly classify the sample, and/or in situations where samples are incompatible with the use of multiple different regional markers.

Figure 2:
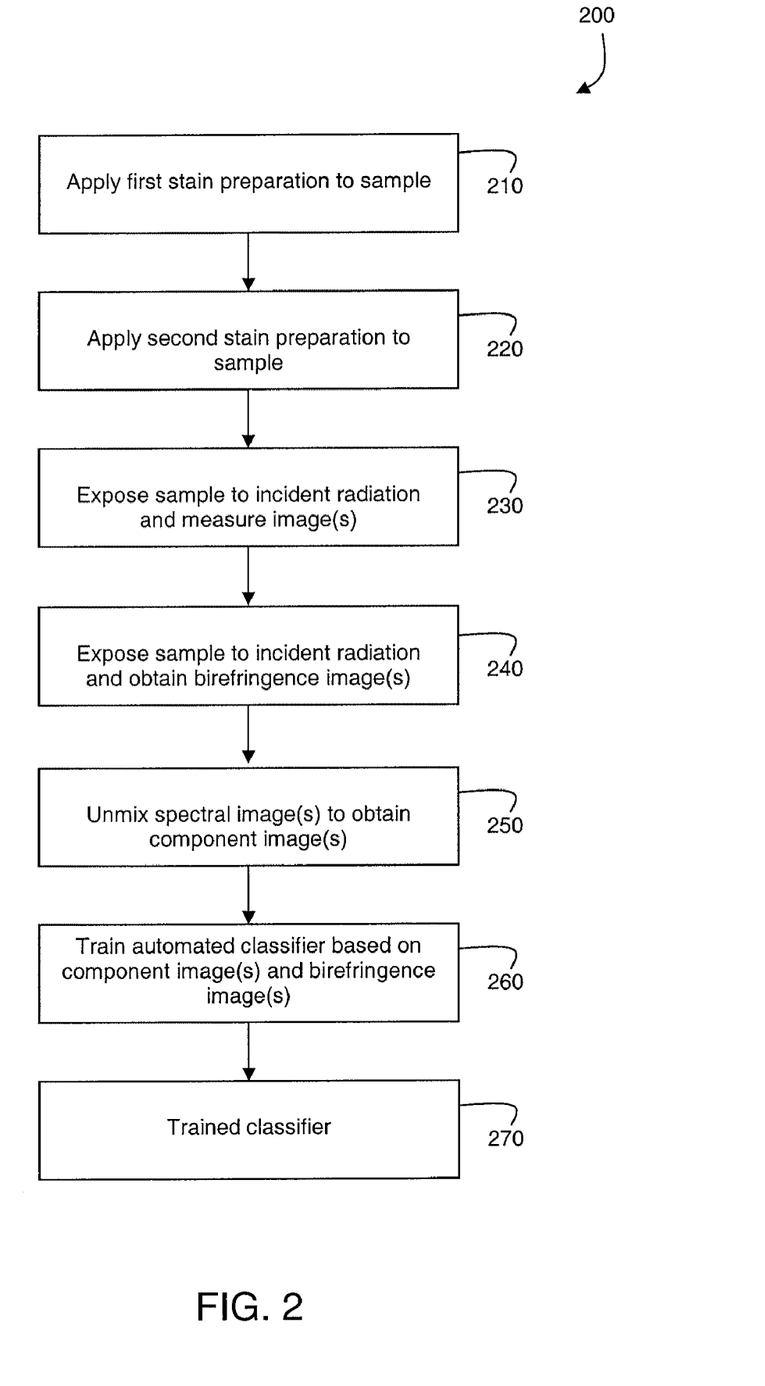
FIG. 2 is a flow chart showing steps in a further procedure used to train an automated classifier.

In certain embodiments, one or more birefringence images of a sample can be used in place of, or in addition to, the one or more regional markers applied in the first stain preparation to train an automated classifier. FIG. 2 shows a flow chart 200 that includes a series of steps that can be used to train an automated classifier using birefringence information. In step 210, a first stain preparation is applied to the sample. In optional step 220, a second stain preparation can be applied to the sample. Then, in step 230, the stained sample is exposed to incident radiation and one or more images of the sample are obtained. The one or more images can include, for example, multispectral images that include a spectral cube of data corresponding to absorption, reflectance, or emission of radiation by the stained sample is obtained. In some embodiments, the one or more images can include one or more color images (e.g., RGB images) that include multiple color channels, each of which can be analyzed separately, as discussed previously. The one or more markers that are applied to the sample in each of the first and second stain preparations in steps 210 and 220, respectively, are typically non-localized stains similar to those discussed previously in connection with the second stain preparation applied in step 120 of the chart shown in FIG. 1.

In step 240, the stained sample is exposed to further incident radiation, and one or more birefringence images of the sample are obtained. In the procedure shown in FIG. 2, the one or more birefringence images of the sample provide information about regions of interest in the sample in a manner similar to the regional markers applied in the first sample preparation discussed in connection with FIG. 1. Birefringence images show image contrast where components of a sample are birefringent. For example, certain sample components such as collagen have natural birefringence that manifests as image intensity modulation in birefringence images. The intensity modulation (e.g., intensity differences with respect to intensities of non-birefringent sample components) can be used to delineate regions of interest in the sample corresponding to the birefringent components.

In optional step 250, the images obtained in step 230 can be unmixed to obtain component images corresponding to each of the one or more non-localized markers applied to the sample in step 210 and optional step 220. In some embodiments, the one or more images obtained in step 230 are not unmixed, and are instead submitted directly to the classifier as "component" images (e.g., if the first stain preparation includes only one or two non-localized markers, and no second stain preparation is applied to the sample).

The component images (which can include non-unmixed images, as discussed above) corresponding to markers applied in the first stain preparation and, optionally, to markers applied in the second stain preparation, are used along with the birefringence image(s) in step 260 to train the classifier. Regions of interest during the training are identified and analyzed based on the birefringence image information, and the classifier is trained by analyzing component images corresponding to the non-localized markers based on the regions of interest. In step 370, a trained automated classifier is obtained. Once trained, the automated classifier can be used as discussed in any of the previous embodiments to analyze samples that have been stained with regional markers, non-localized markers, and mixtures of regional and non-localized markers. The automated classifier can also be used to classify subsequent samples on the basis of one or more birefringence images of the samples in addition to, or as an alternative to, applying any of the regional and/or non-localized markers. Typically, when the automated classifier is trained based on regions-of-interest information derived from one or more birefringence images, the trained classifier can be used to identify and analyze regions of interest in birefringence images of subsequent samples with or without non-localized stains such as counterstains applied to the samples.

A variety of different methods and systems can be used to acquire birefringence images of samples. Exemplary methods and systems are disclosed, for example, in U.S. patent application Ser. No. 11/397,336 to Clifford C. Hoyt et al., filed on Apr. 4, 2006, published as U.S. Patent Application Publication No. US 2007/0231784, the entire contents of which are incorporated herein by reference.

As discussed above, step 220 in flow chart 200 is optional. Typically, one or more additional non-localized stains such as counterstains might be applied where particular sample architectural information is revealed by such stains. Visual review and assessment of classified samples (e.g., by a system operator following classification by the automated classifier) may also be aided by the application of additional non-localized stains in step 220. Even if such stains are applied in step 220, component images corresponding to the stain(s) may not, in some embodiments, be used to train the automated classifier. Instead, component images corresponding to the one or more non-localized markers applied in the first stain preparation in step 210 may be used to train the classifier.

In certain embodiments, rather than applying a second stain preparation to the training sample (including one or more non-localized markers), the automated classifier can be trained based on autofluorescence information obtained from one or more sample images. For example, referring again to FIG. 1, a first stain preparation can be applied to the training sample, the first stain preparation including one or more regional markers as in step 110. The stained sample, without applying a second stain preparation, can then be exposed to radiation, and one or more spectral images of the sample can be obtained in step 130. By unmixing the spectral images in step 140, a component image corresponding to sample autofluorescence can be obtained, along with component images corresponding to each of the different regional markers applied in step 110. One or more of the component images corresponding to the regional markers can be used, along with the autofluorescence image of the sample, to train the classifier in step 150. Because sample autofluorescence is typically emitted from multiple different regions of a sample, the autofluorescence image can perform a function during classifier training that is analogous to component images that correspond to non-localized markers. In step 160, a trained automated classifier is obtained and can be used to classify other samples based on autofluorescence images (or even other types of images), for example.

In certain other embodiments, rather than applying a second stain preparation to the training sample, the automated classifier can be trained based on birefringence information obtained from one or more sample images. For example, referring again to FIG. 1, a first stain preparation can be applied to the training sample, the first stain preparation including one or more regional markers as in step 110. The stained sample, without applying a second stain preparation, can then be exposed to radiation, and one or more spectral images of the sample can be obtained in step 130. A birefringence image is also obtained. By unmixing the spectral images in step 140, a component image is obtained for each of the regional markers applied in step 110. Unmixing can be omitted if the markers are spectrally distinct enough. One or more of the component images corresponding to the regional markers can be used, along with the birefringence image of the sample, to train the classifier in step 150. The birefringence image can perform a function during classifier training that is analogous to component images that correspond to non-localized markers. In step 160, a trained automated classifier is obtained which can be used to classify other samples based on birefringence images.

In some embodiments, information about regions of interest in a sample can be provided and used to train an automated classifier, where such information would otherwise be difficult to obtain by applying certain regional markers to a training sample. For example, one or more regional markers can be applied to a sample in the first stain preparation and component images corresponding to the regional markers can be used to identify regions of interest in the sample. An automated classifier can then be trained based on the identified regions. Images of subsequent samples can then be acquired by methods that are incompatible with staining the sample with the regional markers used in the first stain preparation. Such incompatibilities can arise for a number of reasons, including spectral overlap between markers used in the first stain preparation and markers applied to the subsequent samples, and chemical or biological incompatibilities between markers used in the first stain preparation and markers applied to the subsequent samples. A number of significant advantages can arise from using such a procedure. In some embodiments, for example, the analysis of subsequent samples can including applying a larger number of markers (e.g., non-localized markers) than might otherwise be possible if regional markers were applied to the samples. Further, regional markers that might be incompatible with the regional markers used in the first stain preparation, but which yield useful sample information, can be applied in the analysis of subsequent sample. Further still, by appropriate selection of the markers applied to subsequent samples, spectral channels that would otherwise be dedicated to measurement of contributions from certain regional markers (e.g., those used in the first stain preparation) can be freed and used to obtain additional sample information.

In some embodiments, some of the regions-of-interest information supplied to the automated classifier (e.g., in the form of component images in step 150 of flow chart 100) can be instead supplied directly (e.g., automatically or by a system operator) to the automated classifier to delineate regions of interest in the training sample. The direct provision of information can occur, for example, when particular regions of interest in a sample are optically and/or biochemically incompatible with regional markers. Alternatively, or in addition, regions-of-interest information can be supplied to the automated classifier when the identification of the regions, e.g., by applying regional markers to the sample, would require the application of too many markers, leading to spectral overlap and/or chemical or biological incompatibilities between the applied markers.

In certain embodiments, a classifier can be trained to identify and analyze several different classes of regions of a sample. For example, a classifier can be trained to identify and analyze classes of regions that correspond to multiple different tissue types. Alternatively, a classifier can be trained to identify and analyze classes of regions that correspond to multiple different cell types, multiple different sub-cellular structures, multiple different tissue structures or types (e.g., inflamed tissue and non-inflamed tissue), or multiple different disease states. For example, a regional marker applied to the training sample in the first stain preparation might localize in each of two or more different classes of regions of interest, such as two or more different tissue types. A system operator can intervene in the training process to indicate which of the regions in which the regional marker localizes belong to each class of tissue. Alternatively, or in addition, an electronic processor can apply an algorithm to assign the identified regions into classes (e.g., tissue types) based on criteria such as the positions of the regions, for example.

In some embodiments, the methods disclosed herein can be used to train more than one automated classifier. For example, in some embodiments, the methods disclosed herein can be used to train a first classifier that identifies and analyzes a first type of region in samples, and a second classifier that identifies and analyzes a second type of region. The first classifier can be trained to identify certain types of tissue or certain types of cells or certain types of sub-cellular components of cells. Similarly, the second classifier can be used to identify other types of tissue or cells or sub-cellular components. As another example, a first classifier can be trained to identify a certain type of tissue, and a second classifier can be trained to identify a certain type of cells and/or sub-cellular components. As yet another example, a first classifier can be trained to identify a certain type of cells, and a second classifier can be trained to identify a certain type of sub-cellular components. In general, any number of automated classifiers can be trained to identify a variety of different types of regions, structures, and components of samples.

In certain embodiments, as discussed above, more than one non-localized marker (e.g., counterstain) can be applied to a training sample (e.g., in step 120 of flow chart 100). Multiple non-localized markers can be applied, for example, when multiple classifiers are trained using information derived from a single training sample. As another example, multiple non-localized markers can be applied to highlight certain features of samples and/or to provide additional visual information to a system operator. Typically, the multiple non-localized markers are selected such that they are spectrally distinct, but markers that overlap spectrally can be unmixed using the methods disclosed herein. In step 140 of flow chart 100, for example, if multiple non-local markers are applied to a sample, then spectral unmixing will yield multiple component images corresponding to the non-localized markers. One or more of these component images can be used in step 150 to train an automated classifier, depending upon the nature of the sample images that the automated classifier will be used to analyze.

In the methods and systems disclosed herein, the extent of overlap between regions of the sample to which the regional markers bind and regions to which the non-localized markers bind can vary considerably. For example, in some embodiments, the first stain preparation includes a regional marker that binds to cancerous membranes of cells in a tissue sample. The second stain preparation includes a non-localized marker that binds to nuclei of cells in the tissue sample. Some of the nuclei to which the non-localized marker binds correspond to cancerous cells, and other nuclei do not. Different component images, derived for example by unmixing spectral images of the stained sample and/or by analyzing independent channels of a multi-color sample image, corresponding substantially only to contributions from the regional marker, and from the non-localized marker, respectively, can be used to train an automated classifier to identify and classify cancerous membranes.

As another example, as discussed above, an automated classifier can be trained based on component images corresponding to one or more regional markers applied in the first stain preparation, and based on a component image corresponding to sample autofluorescence which is typically emitted from most or all portions of the sample. The trained classifier can then be used to classify samples based on autofluorescence images of the samples, and/or based on component images corresponding to other non-localized markers (e.g., which typically bind to a large number of non-specific binding sites within samples).

More generally, regional markers (or their functional equivalents, such as sample birefringence) typically bind or correspond to a first subset of regions within a sample. Non-localized markers (or their functional equivalents, such as sample autofluorescence or, in some embodiments, sample birefringence) typically bind or correspond to a second subset of regions within the sample. The first and second subsets of sample regions can, in some embodiments, share almost no regions in common. Alternatively, in certain embodiments, the first and second subsets of sample regions can share one or more regions in common. In some embodiments, the first and second subsets of sample regions can share all or nearly all regions in common. For example, the second subset of sample regions can be a superset that includes all of the first subset of sample regions, and also includes additional sample regions. Further, in certain embodiments, some regions corresponding to the first subset of regions can be positioned adjacent to some regions corresponding to the second subset of regions. For example, as discussed above, a regional marker can be used to stain cell membranes. Portions of the sample that correspond to the cell membranes correspond to the first subset of regions in the sample. A second, non-localized marker can also be applied to the sample, and can bind to regions of the sample such as nuclei which are adjacent to cell membranes. Accordingly, some members of the second subset of sample regions corresponding to the nuclei stained with the non-localized marker can be at least partially adjacent to some members of the first subset of sample regions corresponding to the cell membranes.

The trained classifiers obtained, e.g., in steps 160 and 270 of FIGS. 1 and 2, or following any of the other methods disclosed herein, can be used to identify and classify one or more regions of samples other than the training sample. Typically, although not in all embodiments, the other samples are stained with one or more of the non-localized markers applied to the training sample, one or more images of the stained samples are obtained and submitted to the trained classifier, and the classifier classifies different regions of the samples. In some embodiments, the other samples do not include any of the non-localized stains applied to the training sample; instead, the other samples can include one or more different non-localized stains (e.g., counterstains), and images of the samples can be unmixed to obtain component images corresponding to the applied non-localized stains. Alternatively, or in addition, the other samples can be classified based on one or more autofluorescence and/or birefringence images of the samples.

Machine Hardware and Software

The steps described above in connection with various methods for collecting, processing, analyzing, interpreting, and displaying information from samples, and for training automated classifiers based on information obtained from samples, can be performed by electronic processors (such as computers or preprogrammed integrated circuits) executing programs based on standard programming techniques. Such programs are designed to execute on programmable computers or specifically designed integrated circuits, each comprising a processor, a data storage system (including memory and/or storage elements), at least one input device, and at least one output device, such as a display or printer. The program code is applied to input data to perform the functions described herein and generate output information which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that, when read by a computer, can cause the processor in the computer to perform the analysis and control functions described herein.

Other Embodiments

A number of embodiments have been described. Nevertheless, it will be understood that various modifications may be made without departing from the spirit and scope of the disclosure. Accordingly, other embodiments are within the scope of the following claims.

What is claimed is:

1. A method, comprising:
    applying a first stain to a first sample having a plurality of regions, wherein the first stain selectively binds to only a first subset of the regions of the first sample;
    applying a second stain to the first sample, wherein the second stain binds to a second set of regions of the first sample;
    obtaining an image of the first sample, and analyzing the image to obtain a first component image corresponding substantially only to spectral contributions from the first stain, and a second component image corresponding substantially only to spectral contributions from the second stain; and
    training a classifier to identify regions of a second sample based on information derived from the first and second component images, the identified regions corresponding to the first subset of regions of the first sample.

2. The method of claim 1, wherein the first subset of regions and the second set of regions have regions in common.

3. The method of claim 1, wherein the second set of regions comprises at least some regions that are each adjacent to a region in the first subset.

4. The method of claim 1, wherein the second set of regions is a subset of the regions of the first sample.

5. The method of claim 1, wherein the second set of regions corresponds to substantially all of the first sample.

6. The method of claim 1, wherein the first subset of regions corresponds to membranes in the first sample.

7. The method of claim 1, wherein the second set of regions corresponds to nuclei in the first sample.

8. The method of claim 1, wherein the second set of regions corresponds to non-specific binding sites in the first sample.

9. The method of claim 1, wherein the information derived from the first component image comprises position information corresponding to the first subset of regions.

10. The method of claim 1, wherein the information derived from the first component image comprises information about an amount of the first stain in the first subset of regions.

11. The method of claim 1, wherein the information derived from the second component image comprises information about an amount of the second stain in the second set of regions.

12. The method of claim 1, further comprising applying a third stain to the first sample, wherein the third stain selectively binds to a third subset of the regions of the first sample.

13. The method of claim 12, wherein the first subset of regions and the third subset of regions have regions in common.

14. The method of claim 12, wherein the third subset of regions and the second set of regions have regions in common.

15. The method of claim 12, wherein the second set of regions comprises at least some regions that are each adjacent to a region in the third subset of regions.

16. The method of claim 12, further comprising:
    analyzing the image to obtain a third component image, wherein the third component image corresponds substantially only to spectral contributions from the third stain; and
    training the classifier based on information derived from the third component image.

17. The method of claim 16, wherein the classifier is a first classifier, and further comprising training a second classifier to identify regions of another sample, the identified regions corresponding to the third subset of regions of the first sample.

18. The method of claim 12, wherein one of the first and second stains comprises a fluorogenic stain and the other of the first and second stains comprises a chromogenic stain.

19. The method of claim 1, wherein the second stain comprises a counterstain.

20. The method of claim 1, further comprising applying a fourth stain to the first sample, wherein the fourth stain binds to a fourth set of regions of the first sample.

21. The method of claim 20, wherein the fourth set of regions is a subset of regions of the first sample.

22. The method of claim 20, wherein the fourth set of regions corresponds to substantially all of the first sample.

23. The method of claim 20, further comprising:
    analyzing the image to obtain a fourth component image, wherein the fourth component image corresponds substantially only to spectral contributions from the fourth stain; and
    training the classifier based on information derived from the fourth component image.

24. The method of claim 1, wherein the first subset of regions of the first sample comprises one or more types of tissue.

25. The method of claim 1, wherein the first subset of regions of the first sample comprises one or more types of cells.

26. The method of claim 1, wherein the first stain comprises at least one member of the group consisting of immunohistochemical agents, cytokeratin, and cadherin.

27. The method of claim 1, wherein the second stain comprises at least one member of the group consisting of immunohistochemical agents, DAB, fast red, fluorescein, rhodamine, Texas red, Cy3, Cy5, Cy5.5, Alexa dyes, quantum dots, DAPI, Hoechst blue, and hematoxylin.

28. The method of claim 1, wherein analyzing the image comprises unmixing the image to obtain the first and second component images.

29. The method of claim 1, wherein analyzing the image comprises separating image color channels to obtain the first and second component images.

30. The method of claim 1, wherein a difference between a wavelength of a maximum in a fluorescence emission spectrum of the first stain and a wavelength of a maximum in a fluorescence emission spectrum of the second stain is 50 nm or more.

31. The method of claim 1, wherein a difference between a wavelength of maximum absorption of the first stain and a wavelength of maximum absorption of the second stain is 50 nm or more.

32. The method of claim 1, further comprising obtaining birefringence information about the first sample, and training the classifier based on the birefringence information.

33. The method of claim 32, wherein the birefringence information comprises one or more birefringence images of the first sample.

34. The method of claim 1, further comprising providing position information corresponding to the first subset of regions of the first sample to the classifier to train the classifier.

35. The method of claim 34, wherein the position information comprises an image of the first sample that does not correspond to spectral contributions from the first stain.

36. The method of claim 35, wherein the position information comprises texture information derived from the image of the first sample.

37. The method of claim 36, wherein the second stain comprises a counterstain.

38. The method of claim 1, wherein obtaining the image comprises exposing the first sample to incident radiation and detecting emitted radiation from the first sample, the emitted radiation corresponding to fluorescence emission from the first sample, reflected incident radiation from the first sample, or transmitted incident radiation from the first sample.

39. The method of claim 1, further comprising using the trained classifier to identify the regions of the second sample.

40. The method of claim 39, wherein using the trained classifier comprises using the trained classifier to identify the regions of the second sample when the second sample is not stained with the first stain.

41. The method of claim 1, wherein training the classifier comprises training the classifier to identify regions of the second sample when the second sample is not stained with the first stain.

42. A method, comprising:
applying a stain to a first sample having a plurality of regions, wherein the stain selectively binds to a first set of regions of the first sample;
obtaining an image of the first sample, and analyzing the image to obtain a component image corresponding substantially only to spectral contributions from the stain;
obtaining a birefringence image of the first sample; and
training a classifier to identify regions of a second sample based on information derived from the component image and the birefringence image.

43. The method of claim 42, wherein the first set of regions is a subset of the regions of the first sample.

44. The method of claim 42, wherein the first set of regions corresponds to substantially all of the first sample.

45. The method of claim 42, wherein the birefringence image comprises a set of regions corresponding to a second subset of the regions of the first sample, the second subset of regions of the first sample having optical retardance values that are different from optical retardance values of other regions of the first sample.

46. The method of claim 45, wherein the second subset of regions and the first set of regions have regions in common.

47. The method of claim 45, wherein the first set of regions comprises at least some regions that are each adjacent to a region in the second subset of regions.

48. The method of claim 45, wherein the second subset of regions corresponds to membranes in the first sample.

49. The method of claim 45, wherein the second subset of regions corresponds to nuclei in the first sample.

50. The method of claim 45, wherein the information derived from the birefringence image comprises position information corresponding to the second subset of regions.

51. The method of claim 45, wherein the second subset of regions comprises one or more types of tissue.

52. The method of claim 45, wherein the second subset of regions comprises one or more types of cells.

53. The method of claim 45, wherein the second subset of regions comprises one or more types of sub-cellular components.

54. The method of claim 42, wherein the stain comprises a counterstain.

55. The method of claim 42, wherein analyzing the image comprises unmixing the image to obtain the component image.

56. The method of claim 42, wherein analyzing the image comprises separating image color channels to obtain the component image.

57. The method of claim 42, further comprising:
applying a second stain to the first sample, wherein the second stain binds to a third set of regions of the first sample;
analyzing the image to obtain a second component image corresponding to the second stain; and
training the classifier based on information derived from the second component image.

58. The method of claim 42, further comprising using the trained classifier to identify the regions of the second sample.

59. The method of claim 58, wherein using the trained classifier comprises using the trained classifier to identify the regions of the second sample when the second sample is not stained with the stain applied to the first sample.

60. The method of claim 42, wherein training the classifier comprises training the classifier to identify regions of the second sample when the second sample is not stained with the stain applied to the first sample.

61. The method of claim 42, wherein the stain comprises at least one member of the group consisting of immunohistochemical agents, cytokeratin, and cadherin.

62. A method, comprising:
applying a stain to a first sample having a plurality of regions, wherein the stain selectively binds to only a first subset of the regions of the first sample;
obtaining an image of the first sample, and analyzing the image to obtain a first component image corresponding substantially only to spectral contributions from the first stain, and a second component image corresponding substantially only autofluorescence contributions from the sample; and
training a classifier to identify regions of a second sample based on information derived from the first and second component images, the identified regions corresponding to the first subset of regions of the first sample.

63. The method of claim 62, further comprising applying a second stain to the first sample, wherein the second stain selectively binds to a second subset of the regions of the first sample.

64. The method of claim 63, further comprising:
analyzing the image to obtain a third component image, wherein the third component image corresponds substantially only to spectral contributions from the second stain; and
training the classifier based on information derived from the third component image.

65. The method of claim 62, wherein the information derived from the first component image comprises position information corresponding to the first subset of regions.

66. The method of claim 62, wherein the information derived from the first component image comprises information about an amount of the first stain in the first subset of regions.

67. The method of claim 62, further comprising using the trained classifier to identify the regions of the second sample.

68. The method of claim 67, wherein using the trained classifier comprises using the trained classifier to identify the regions of the second sample when the second sample is not stained with the stain applied to the first sample.

69. The method of claim 62, wherein training the classifier comprises training the classifier to identify regions of the second sample when the second sample is not stained with the stain applied to the first sample.

70. The method of claim 62, wherein the stain comprises at least one member of the group consisting of immunohistochemical agents, cytokeratin, and cadherin.

\* \* \* \* \*